United States Patent [19]

Kusz et al.

[11] 4,026,656
[45] May 31, 1977

[54] STONE DETECTOR

[75] Inventors: Maximillian Kusz, Maumee; Sam Lovalenti, Toledo, both of Ohio

[73] Assignee: Owens-Illinois, Inc., Toledo, Ohio

[22] Filed: Sept. 2, 1975

[21] Appl. No.: 609,325

[52] U.S. Cl. .............................. 356/51; 250/223 B; 250/338; 250/341; 356/33; 356/240
[51] Int. Cl.$^2$ ................. G01N 21/34; G01N 21/32
[58] Field of Search ............. 356/51, 237, 240, 33; 250/223 B, 341, 338, 225; 209/111.7

[56] References Cited

UNITED STATES PATENTS

| | | | |
|---|---|---|---|
| 1,681,991 | 8/1928 | Littleton, Jr. | 250/225 |
| 1,934,187 | 11/1933 | Glasgow et al. | 356/33 |
| 2,798,605 | 7/1957 | Richards | 356/240 |
| 3,411,005 | 11/1968 | Taylor | 350/338 |

Primary Examiner—Vincent P. McGraw
Attorney, Agent, or Firm—Steve M. McLary; E. J. Holler

[57] ABSTRACT

An improved device for detection of stones in the sidewalls of glass containers. Stones in the sidewalls of glass containers cause stress patterns to be formed. These patterns are visible if the glass container is viewed through crossed polarizing filters due to the refraction of polarized light. A television camera and electronic analysis circuit may be substituted for the human eye. The detection capability and reliability of the system is improved if the glass container is illuminated with primarily infra-red radiation. Then, polarizing filters which polarize infra-red radiation and remove visible light are used. A filter before the television camera lens removes far infra-red radiation and allows only near infra-red radiation to be measured. This makes the device insensitive to glass color, flutes or stippling and improves the signal to noise ratio.

5 Claims, 2 Drawing Figures

4,026,656

STONE DETECTOR

BACKGROUND OF THE INVENTION

This invention generally relates to the inspection of glass containers. More particularly, this invention relates to the inspection of glass containers for sidewall flaws using a television camera as a sensing element. Specifically, this invention relates to the inspection of glass containers for stress inducing sidewall inclusions by the use of polarized infra-red radiation.

It has long been known that stresses in glass containers could be seen by viewing the glass container through crossed polarizing filters. Solid inclusions in the sidewalls of glass containers are generally referred to as "stones". This general term is used regardless of the source of the inclusion. Stones in the sidewalls of glass containers create stress patterns which can be seen when the polarizing filters are used. The following paper suggested the use of a television camera and polarized illumination to detect stones in glass containers: "Automatic Stone Detector With Closed Circuit TV", M. Watonabe, Y. Ito, S. Nakatani, IFAC Symposium on Automatic Control in Glass, Lafayette, Indiana, 25-28, September, 1973, (Pittsburgh, Pa.: ISA 1973), p. 196-201. However, this system has not proven to be completely satisfactory because of ambient light interference problems, glass color problems, and glass surface texture interference. We have found that the use of polarized infra-red radiation will eliminate visible light problems, but still allow viewing of sidewall stresses caused by stones. Other examples of the prior art may be seen in the following U.S. Pat. Nos. 2,649,500; 2,798,605; 3,379,829; 3,565,536; 3,576,442; 3,746,784; and 3,894,806.

SUMMARY OF THE INVENTION

Our invention resides in a method and apparatus for the inspection of glass containers for the presence of stress inducing sidewall inclusions. In the basic apparatus, the glass container is illuminated by linearly polarized, infra-red radiation. The illuminated glass container is viewed through a polarizing medium, with its axis set at 90° with respect to the axis of polarization of the illumination, by a television camera. An electronic means is designed to analyze the output signal of the television camera to determine whether or not an inclusion is present in the sidewall of the glass container. The apparatus further includes a means for moving the glass containers in a spaced apart, single file to and through an inspection zone. Finally, a means for filtering all radiation passing to the television camera to remove all radiation having a wavelength greater than 9500 A is provided. This results in the television camera seeing radiation only in a range of 7000 A to 9500 A.

DETAILED DESCRIPTION OF THE DRAWINGS

Figure 1:
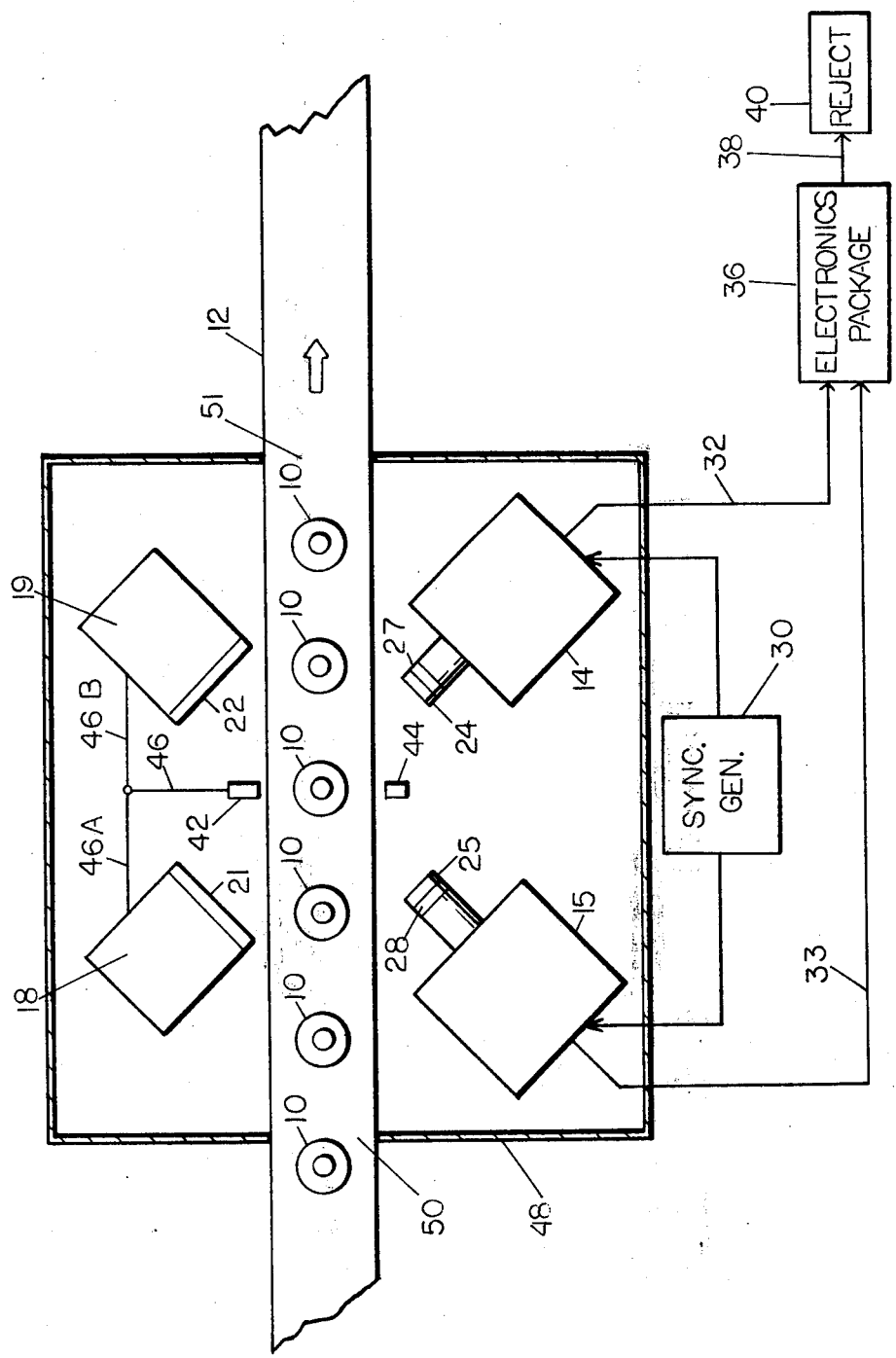
FIG. 1 is a schematic, top plan view of the apparatus of the present invention.

Glass containers 10 which are to be inspected are moved in a continuous, generally evenly spaced, single file by a continuously moving endless conveyor 12. At the desired location, where the glass containers 10 are to be inspected, two television cameras 14 and 15 are positioned at substantially right angles to one another to view a single glass container 10. The television cameras 14 and 15 may be GBC-CTC 6000 models. This camera is manufactured by the GBC Closed Circuit TV Corporation, 74 5th. Avenue, New York, N. Y. 10011. These cameras are of the type which are sensitive to infra-red radiation. Two cameras are used to obtain coverage of substantially the entire surface area of the glass container 10. A single camera, however, could be used with some sacrifice in accuracy. A single camera with an appropriate optical system using mirrors and prisms could also be used to view the entire surface. The glass container 10 which is to be inspected at this point is illuminated by light sources 18 and 19 which are also positioned at right angles to one another and facing the television cameras 14 and 15. One important attribute of the light sources 18 and 19 is that they have a high component of infra-red radiation in their output spectrum. Preferably, this infra-red radiation should lie in a range of about 7000 to 9500 A. The light sources 18 and 19 may be continuously operating light sources, but preferably, these are EG & G, model FX5C-9 Xenon flash tubes. These tubes are manufactured by EG & G Incorporated, 35 Congress Street, Salem, Mass. 01970. It may be useful to mask off part of the face of the light sources 18 and 19 to more precisely illuminate the glass container 10 which is being inspected. In addition, a diffusing screen may be placed in front of each of the light sources 18 and 19. Each of the light sources 18 and 19 have placed in front of them a polarizing filter 21 and 22 respectively. The polarizing filters 21 and 22 are preferably a type HN ½ manufactured by the Polaroid Corporation. This type of material is specifically designed to polarize infra-red type radiation and will not pass radiation in the visible light range. Each of the television cameras 14 and 15 have placed before their lenses a second polarizing filter 24 and 25, respectively, which are identical to the polarizing filters 21 and 22 except turned at 90° with respect to the axis of the filters 21 and 22. The result of this configuration of polarizing filters is that light which passes through a perfect glass container 10 will be completely filtered and will not enter the television cameras 14 and 15. Additionally, the television cameras 14 and 15 have cut off filters 27 and 28 also placed in front of their lenses. The cut off filters are designed to block infra-red radiation above 9500 A from entry into the television cameras 14 and 15. Since the light sources 18 and 19 are designed to primarily furnish infra-red radiation as the measuring light source, cutting out all visible light will improve the signal to noise ratio and also prevent the generation of spurious signals. Generally, one considers the visible spectrum to end at about 7000 A. The particular strobe sources which are used have light peaks at 8000 A and at 9000 A. The filters 27 and 28 may be dielectric filters with an 8700 A cut off. Thus, the majority of radiation above 8700 A is blocked from entry into the television cameras 14 and 15. However, since there is a peak at 9000 A, other filters could be used which would have a cut off in the range of about 9200 since appreciable infra-red radiation is available at this wavelength. Likewise, it would be possible to move the cut off filter frequency back to take advantage of the 8000 A peak of the flash tubes. A synchronizing generator 30 is used to maintain the two television cameras 14 and 15 in synchronization so that both are looking at the same picture at the same time. The output signal from the cameras 14 and 15 is transmitted along conductors 32 and 33 respectively to an electronics package 36. The electronics package may be essentially identical to that shown in U.S. Pat. No. 3,746,784. If the determination is made that a defective glass container 10 has been found, a signal is generated along an output conductor 38 and sent to a rejection mechanism 40 to allow removal of the glass container 10 from the stream of glass containers moving along the conveyor 12. If the light sources 18 and 19 are strobe lights, as in the preferred embodiment, it is useful to control the cycling of these lights so that they are on at the time that the glass container 10 is in the proper location for viewing by the television cameras 14 and 15. To this end, a retro-reflective type photosensor 42 may be used as a sensing means. The sensor 42 sends a light beam across the conveyor 12 to a retro-reflector 44. When a glass container 10 blocks this light path, a signal is generated which is sent along a conductor 46 and then along branch conductors 46a and 46b to trigger the light sources 18 and 19 to flash at this particular time. This allows stop motion viewing of the glass container under inspection. At the time the retro-reflector 44 is blocked, the glass container 10 is positioned so that the television cameras 14 and 15 can see substantially its entire curcumference. The light sources 18 and 19, television cameras 14 and 15, and sensor 42 thus generally define an inspection zone. It is possible for infra-red radiation from the surrounding to interfere with proper operation of this device. This depends upon the environment, and does not occur in all cases. However, when this interference is present, the entire inspection zone may be enclosed with a hood 48. The hood 48 has entrance and exit openings 50 and 51 to allow passage of the glass container 10.

Figure 2:
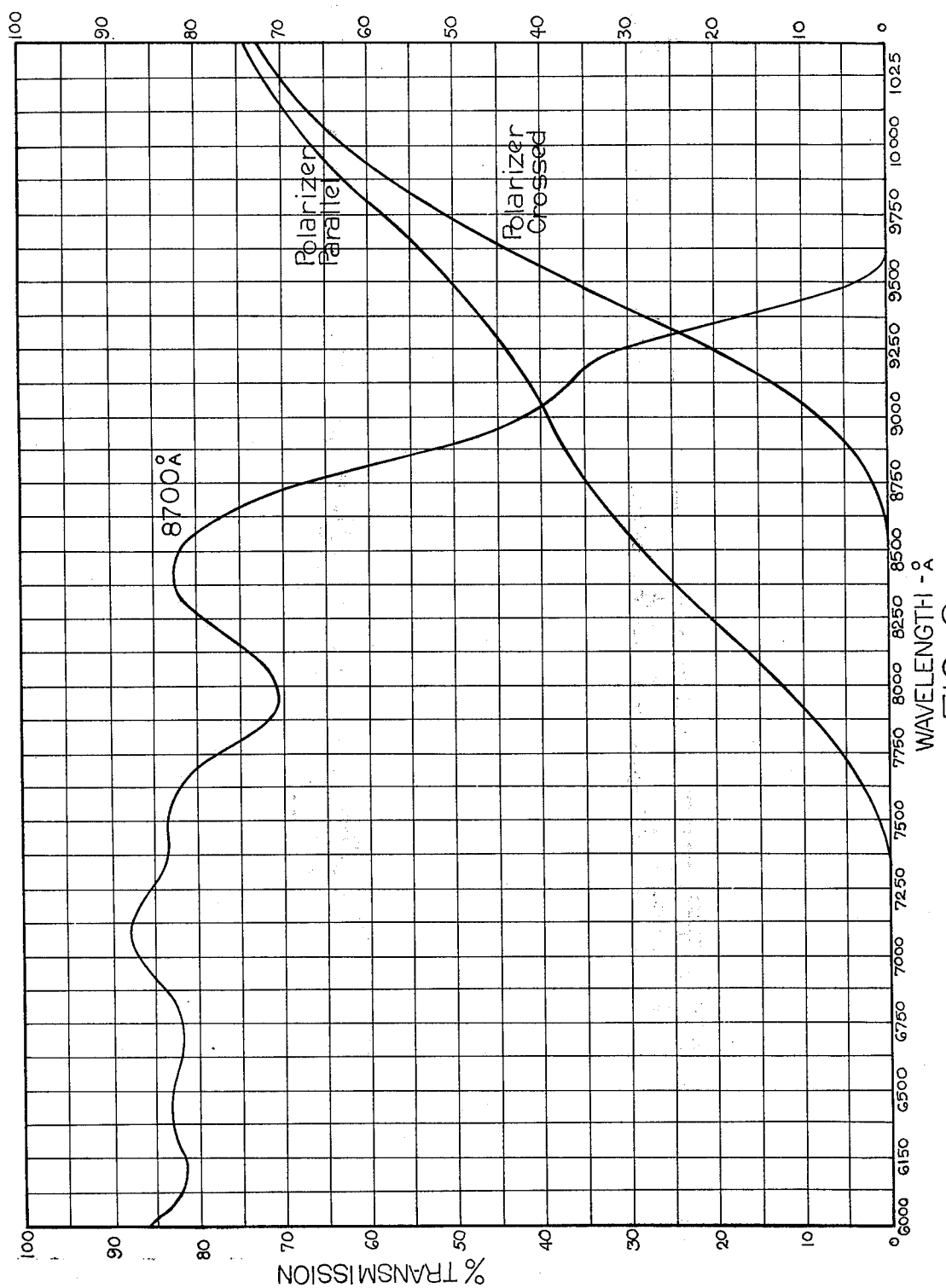
FIG. 2 is a plot of transmission as radiation wavelength for three filters of the present invention.

The basic operating principles of this invention may be better understood with reference to FIG. 2. The use of infra-red radiation makes the entire system insensitive to glass color, flutes in the glass, surface stippling or other surface texture or features. The transmission vs. wavelength curve of the cut off filter is designated as 8700 A in FIG. 2. This filter will pass visible light, but by 9750 A passes essentially no radiation. The polarizers alone, designated as "polarizer parallel" in FIg. 2, will not pass visible light, but will pass infra-red radiation. This explains the possible need for the hood 48. Visible light is blocked from the cameras by the polarizers 24 and 25 alone, but ambient infra-red can still be passed. Finally, with the polarizers set at 90° to one another, shown as "polarizer crossed" in FIG. 2, which is the actual operational condition, a wavelength bandpass zone is created. Note that only under the area defined by where the 8700 A and the polarizer crossed curves in FIG. 2 can any infra-red radiation reach the cameras 14 and 15. It should be carefully noted that the curves of FIG. 2 are only light transmission curves and have no bearing whatsoever on the polarizing effects. That is an entirely different question altogether. Basically, a viewing window in the near infra-red has been created to obtain the benefits of this type of inspection using infra-red radiation. Thus, only infra-red radiation from the light sources are polarized and used as the measuring medium, with the cut off filters serving to prevent interference from far infra-red radiation. Stating the matter somewhat differently, FIG. 2 shows that beyond 8500 A, the polarizing filters begin to lose their polarizing effect and start to transmit radiation. The cut off filter thus establishes a measuring wavelength range in which the infra-red radiation used is still substantially polarized by the polarizing filters.

What we claim is:

1. A method for the inspection of glass containers for the presence of stress inducing inclusions in the sidewalls thereof which comprises the steps of:
    moving said glass containers in a uniformly spaced apart single file through an inspection zone;
    illuminating said glass containers in said inspection zone with linearly polarized infra-red radiation having a wavelength greater than 7000 A;
    viewing said illuminated glass containers through a polarizing medium, set at 90° with respect to the direction of polarization of said illumination, with a television camera in said inspection zone;
    filtering the radiation passing to said television camera to remove all radiation wavelengths greater than 9500 A; and
    electronically measuring the output of said television camera to determine the presence of inclusions in said glass containers.

2. The method of claim 1 wherein the step of illuminating said glass containers further includes the steps of:
    positioning two flash tubes on the same side of said glass containers; and
    activating said flash tubes in response to the presence of a glass container before said flash tubes.

3. Apparatus for the inspection of glass containers for the presence of stress inducing sidewall inclusions which comprises, in combination:
    means for moving said glass containers in a spaced apart, single file to and through an inspection zone;
    means for illuminating said glass containers, in said inspection zone, with linearly polarized infra-red radiation having a wavelength greater than 7000 A;
    a television camera, responsive to infra-red radiation, positioned in said inspection zone to view said illuminated glass containers;
    a polarizing medium, placed in front of said television camera, having its axis set at 90° with respect to the axis of polarization of said illumination means;
    means for filtering the radiation reaching said television camera to remove all radiation having a wavelength greater than 9500 A; and
    electronic means for analyzing the output of said television camera to determine whether or not an inclusion is present in the sidewall of said glass containers.

4. The apparatus of claim 3 wherein said glass containers are illuminated by at least two flash tubes positioned on one side of said means for moving said glass containers, said flash tubes having an output radiation peak at a wavelength between 7000 A and 9500 A.

5. The apparatus of claim 4 which further includes:
    means for sensing the presence of a glass container before said flash tubes and for firing said flashtubes in response thereto.

* * * * *